United States Patent [19]  [11] 3,974,036
Snell [45] Aug. 10, 1976

[54] PROCESS FOR CONDITIONING BACTERIAL CELLS CONTAINING GLUCOSE ISOMERASE ACTIVITY

[75] Inventor: Raymond Lee Snell, Elkhart, Ind.

[73] Assignee: Miles Laboratories, Inc., Elkhart, Ind.

[22] Filed: July 7, 1975

[21] Appl. No.: 593,257

Related U.S. Application Data

[63] Continuation-in-part of Ser. No. 502,619, Sept. 3, 1974, abandoned.

[52] U.S. Cl. .................................... 195/65; 195/31 F
[51] Int. Cl.$^2$ ............................................ C12B 1/00
[58] Field of Search .................... 195/65, 31 F, 115

[56] References Cited
UNITED STATES PATENTS

| | | | |
|---|---|---|---|
| 3,817,832 | 6/1974 | Lloyd et al. | 195/31 F |
| 3,847,741 | 11/1974 | Heady et al. | 195/31 F |
| 3,868,304 | 2/1975 | Messing | 195/31 F |

*Primary Examiner*—Lionel M. Shapiro
*Attorney, Agent, or Firm*—Louis E. Davidson

[57] ABSTRACT

Bacterial cells having glucose isomerase activity are properly conditioned prior to use to produce a fructose-containing product by (a) mixing the cells with water or an aqueous dextrose solution under controlled conditions until the cells are properly hydrated and pH equilibrated and then (b) passing water or an aqueous dextrose solution up through a bed of such cells under controlled conditions until the effluent solution is clear and is stabilized at desired characteristics. When water is used in step (b), it is followed by the step of passing an aqueous dextrose solution up through the bed until the effluent solution has the same dextrose content as the entering dextrose solution.

6 Claims, No Drawings

PROCESS FOR CONDITIONING BACTERIAL CELLS CONTAINING GLUCOSE ISOMERASE ACTIVITY

This application is a continuation-in-part of application Ser. No. 502,619, filed on Sept. 3, 1974, now abandoned.

BACKGROUND AND PRIOR ART

It is known that a glucose isomerase enzyme can be employed to catalyze the conversion of glucose (dextrose) to fructose (levulose) which has a higher sweetening power than the starting material. Glucose isomerase is also known to be produced by cultivation of various bacteria, such as Streptomyces flavovirens, Streptomyces echinatur, Streptomyces achromogenus, Streptomyces albus, Streptomyces olivaceus and the like, in appropriate nutrient media. The glucose isomerase is primarily formed inside the bacterial cells which grow during its production. Some strains produce a substantial amount of extracellular enzyme. It is generally preferred that there be neglegible extracellular enzyme activity. The cells can then be filtered off from the fermentation beer and used directly as a source of glucose isomerase.

It is desirable that the bacterial cells having glucose isomerase activity be capable of being used in a continuous process for isomerization of glucose to fructose. Various techniques are disclosed in the prior art for immobilization of the enzyme so that it can be reused in a continuous process. One preferred technique is to treat the bacterial cells with glutaraldehyde. This treatment immobilizes the glucose isomerase within the cells and enables the cells to be employed in a stirred reactor or in an isomerization column. It has been found, however, that unless the bacterial cells having immobilized glucose isomerase activity have been properly conditioned prior to their use as isomerization catalysts they will have unsatisfactory physical stability impairing the hydraulic characteristics of the column, the resulting isomerized syrup might have undesirable color and the enzyme life can be undesirably reduced.

SUMMARY OF THE INVENTION

In accordance with the present invention, a process is provided for conditioning bacterial cells having glucose isomerase activity for subsequent use to produce a fructose-containing product which comprises (a) mixing the bacterial cells at about 10°–27°C. with water or an aqueous dextrose solution at a pH of about 8 measured at 25°C. until the cells are hydrated and pH equilibrated; and (b) passing an aqueous dextrose solution up through a bed of such bacterial cells at a temperature of about 60°C. and at a pH of 7.5–8.0 measured at 60°C. until the effluent solution is clear and the pH thereof is stabilized at 7.5–8.0 measured at 60°C.; or passing water at a temperature of about 10°–27°C. and at a pH of 8.0 measured at 25°C. up through a bed of such bacterial cells until the effluent solution is clear and the pH thereof is stabilized at 8.0 measured at 25°C., followed by the step of passing an aqueous dextrose solution up through the bed at a temperature of about 60°C. until the effluent solution has the same dextrose content as the entering dextrose solution.

DESCRIPTION OF THE INVENTION

The bacterial cells having glucose isomerase activity useful in the present invention can be produced by well-known procedures. The preferred enzyme-containing cells are produced by growing under submerged aerobic conditions a culture of Streptomyces olivaceus NRRL 3583 or mutants thereof in a medium containing appropriate nutrients. The resulting bacterial cells are separated from the fermentation beer by filtration or centrifugation.

Various well-known techniques can be employed to immobilize the glucose isomerase. In a preferred technique the recovered bacterial cells are suspended in an aqueous medium and are mixed with glutaraldehyde in an amount from about 0.1 to about 50 weight percent based on the dry weight of the cells.

Since the enzyme-containing treated bacterial cells are usually produced at a different location and at an earlier time than when needed to produce isomerized syrup, the cells are conveniently dried for storage and shipment. Such drying to a moisture content of about 3–10 weight percent can be carried out in any convenient dryer at a temperature of about 60°–70°C. The resulting agglomerated dried cells are then properly sized for subsequent use in a column bed. The agglomerated dried cell mass is conveniently broken into smaller pieces with minimal stress on the individual cells, and the pieces are collected on sieves to obtain a fraction that is retained on a 60 mesh screen and that passes through a 20 mesh screen.

When the so-prepared agglomerates of bacterial cells are to be used in the production of fructose-containing syrup from dextrose, it has previously been the practice to place the cells in a column and start passing the dextrose solution down through the column under the desired temperature and pH conditions. Generally, it takes a significant amount of time before the isomerization reaction stabilizes to a relatively constant state. During this time the resulting isomerized syrup has undesirable color. It has also been found that the useful life of the cells is undesirably short.

In accordance with the present invention, the cells are first mixed with water or with an aqueous dextrose solution. This latter solution can consist of dextrose dissolved in water. Preferably, it consists of a saccharified high dextrose solution produced by enzymatic conversion of starch. The dextrose solution should contain about 30 to 50 weight percent dissolved solids, and such solids should contain about 93 to 96 weight percent dextrose. This dextrose solution also has a Dextrose Equivalent of about 97–98. This water or dextrose solution is employed in an amount of about 10 weight parts per weight part of dried cells. The water or dextrose solution also has a temperature of about 10–27°C. This water or dextrose solution also should contain about 0.0005 Molar concentration of cobalt, such as cobalt chloride, about 0.005–0.007 Molar concentration of magnesium, such as magnesium hydroxide, and about 0.01 Normal concentration of a chelating and buffering agent, such as citric acid. Citric acid is preferred since it forms a soluble chelate complex with the cobalt and magnesium ions and it assists in buffering the water or dextrose solution at the desired pH. This water or dextrose solution should have a pH of 8 measured at 25°C. and such pH is conveniently achieved by addition of appropriate amount of sodium hydroxide. The cells and water or dextrose solution are maintained in contact with minimal agitation for about 1 hour to allow the cells to become properly hydrated and pH equilibrated.

The slurry of cells and water or dextrose solution resulting from the above step is then transferred to a suitable jacketed reactor column to form a bed having a settled depth of about 35–40 in. (89–100 cm.). Minimum agitation of the slurry should be employed to reduce any mechanical injury to the cell agglomerates. In one form of the invention a dextrose solution having the same composition as the dextrose solution described above having a pH of 7.5–8.0 measured at 60°C. is passed at about 60°C. up through the cell bed at a rate of about 1.3 – 1.5 gal./sq. ft. of bed cross-sectional area/min. (53–61 liters/sq. meter of bed cross-sectional area/min.). This is a flow rate that produces about 50–60 volume percent expansion of the settled volume of the cell agglomerates. It also accomplishes desired classification and rearrangement of the cell agglomerates. Once the dextrose solution starts to enter the bed, suitable heating fluid at 60°C. is passed through the column jacket. The effluent solution from the top of the column has a significant amount of color bodies, because it contains various residues from the bacterial cells. The hot dextrose solution should be passed up through the column until the outflow becomes clear and until the effluent pH stabilizes at 7.5–8.0 measured at 60°C. This requires about 2 – 3 bed volumes of solution per hour for about 1 – 3 hours. The dextrose solution flow is then stopped and the cell bed is allowed to settle. In order to reduce the amount of dextrose solution needed for such conditioning, most of the dextrose solution effluent, other than the initial highly colored material, can be recycled through the column. The pH of the recycled material must be adjusted to 7.5–8.0 measured at 60°C. by addition of alkali prior to reuse. In an alternative form of the invention, the cells in the reactor column are initially treated by passing a water solution having the same composition as the water solution described above at a temperature of about 10°–27°C. and at a pH of 8.0 measured at 25°C. up through the cell bed until the effluent solution is clear and the pH thereof is stabilized at 8.0 measured at 25°C., followed by the step of passing an aqueous dextrose solution having the same composition as the dextrose solution described above up through the bed at about 60°C. and at a pH of 7.5–8.0 measured at 60°C. until the effluent solution has the same dextrose content as the entering dextrose solution.

During the above treatment, the water solution and the aqueous dextrose solution are recycled through the bed. The pH of the recycled material is adjusted to the desired level by addition of alkali prior to reuse.

All of the dextrose solutions that come into contact with the bacterial cells having glucose isomerase activity will contain some fructose formed by an isomerization reaction. Therefore, the dextrose solutions used in the above conditioning steps can be decolorized with carbon treatment, demineralized with ion-exchange materials and subsequently employed as components of fructose-containing products.

The cells conditioned by the above process can then be employed in a well-known manner to produce isomerized syrup. A dextrose solution having the above-described composition can flow down through the bed at a pH of about 8 and at a temperature of about 60°C. to produce a product containing about 42–48 weight percent fructose depending on the flow rate. Cell agglomerates conditioned in accordance with the present invention possess an unexpectedly high physical stability and good hydraulic characteristics ideally suited to use in relatively deep beds (30–40 in. or 76–102 cm.). In contrast, the cells treated in accordance with prior art techniques must be limited to use in shallow beds (about 0.5–4 in. or 1.3–10.2 cm.) with extremely large surface area.

The invention will be described in further detail in the following examples.

EXAMPLE 1

A fermentation beer containing Streptomyces olivaceus NRRL 3583 bacterial cells was obtained by culturing such cells in a xylose-containing medium in a known manner. The fermentor beer was then adjusted to a pH of 8.2 by addition of sodium hydroxide. A 1 percent (weight/volume basis) aqueous solution of glutaraldehyde was added to the fermentator beer in an amount of 7 weight percent glutaraldehyde based on the dry weight of the cells in the beer. The resulting mixture was stirred for 1½ hr. during which time sodium hydroxide was added to maintain the pH at 8.2. The cells were then filtered, washed at pH 8 and then dried at 60°–70°C. to a moisture content of 3–10 weight percent. This dried filter cake of agglomerated cells was then broken, and the broken pieces were collected on sieves to obtain a fraction that was retained on a 60 mesh screen and which passed through a 20 mesh screen. The resulting properly sized dried agglomerates of bacterial cells containing immobilized glucose isomerase were then stored at room temperature for further use.

A 300 gm. portion of the above stored cells was mixed with an aqueous dextrose syrup produced by enzyme treatment of starch. This syrup had a Dextrose Equivalent of 97 and contained 30 weight percent dissolved solids, such solids containing 94 weight percent dextrose. This syrup was at a temperature of 10°–27°C. and was employed in an amount of 10 weight parts per weight part of dried cells. This syrup also contained about 0.0005 Molar concentration of cobalt chloride, about 0.005–0.007 Molar concentration of magnesium hydroxide and about 0.01 Normal concentration of citric acid. Sufficient sodium hydroxide was also added to maintain the pH of the dextrose syrup at 8 measured at 25°C. The cells were maintained in contact with the dextrose solution for about 1 hour to allow the cells to become properly hydrated and to become pH equilibrated.

The resulting slurry of cells and dextrose solution was then transferred to a suitable jacketed 1.5 in. dia. reactor column to form a cell bed having a settled depth of about 35–40 in. (89–100 cm). Minimum agitation of the slurry was employed in order to reduce any mechanical injury to the hydrated cells. Dextrose solution having the same composition described above having a pH of 7.5–8.0 measured at 60°C. up through the cell bed at a rate of 1.3–1.5 gal./sq.ft. of bed cross-sectional area/min. (53–61 liters/sq. meter of bed cross-sectional area/min.). Once the dextrose solution started to enter the bed, suitable heating fluid at 60°C. was passed through the jacket of the column. The hot dextrose solution was passed up through the column for about 1 hour until the outflow was clear and until the effluent pH was stabilized at 7.5–8.0 measured at 60°C. The dextrose solution flow was then stopped and the cell bed was allowed to settle for about 15–20 min. During the above conditioning process, the dextrose solution was recycled through the cell bed. The pH of the dextrose solution being recycled was maintained at 7.5–8.0 mesured at 60°C. by the addition of sodium hydroxide. If the pH would be allowed to drop below about 7 measured at 60°C. during the conditioning, physical damage to the cell agglomerates would result.

The cell bed was then ready for use to isomerize dextrose to fructose. A dextrose solution having the same composition described above was allowed to flow downward by gravity under a head pressure of about 4–6 in. (10.2 –15.2 cm.) of solution through the above bed at a temperature of 60°C. at a rate of about 1.5 bed volumes per hour. This is a flow rate of about 0.54 gal./sq. ft. of bed cross-sectional area/hr. (22 liters/sq. meters of bed cross-sectional area/hr.). The pH of the dextrose solution was maintained at 8 measured at 60°C. by addition of sodium hydroxide. An isomerized syrup containing about 42–43 weight percent fructose (based on the weight of the dissolved solids), having no color and containing no psicose was produced. When the flow rate of the dextrose syrup was changed to 1.1 bed volumes per hour (0.4 gal./sq. ft./hr. or 16.3 liters/sq. m./hr.), a product containing about 45–46 weight percent fructose (based on the weight of the dissolved solids), having no color and containing no psicose was produced.

The above cell bed was employed continuously for isomerization for over 1000 hours and the activity of the cell agglomerates was reduced only slightly. Prior art cells which had not been conditioned in accordance with the present invention would lose at least half of their enzyme activity after about 500–600 hours of continuous use.

EXAMPLE 2

A 300 gm. portion of properly sized dried agglomerates of bacterial cells containing immobilized glucose isomerase was produced in accordance with the introductory portion of Example 1. A water solution containing about 0.0005 Molar concentration of cobalt chloride, about 0.005–0.007 Molar concentration of magnesium hydroxide, about 0.01 Normal concentration of citric acid and sufficient sodium hydroxide to maintain the pH at 8 measured at 25°C. was prepared. The dried cells were then mixed with this water solution at 10°–27°C. in an amount of 10 weight parts of water solution per weight part of dried cells. The cells were maintained in contact with the water solution for about 1 hour to allow the cells to become properly hydrated and to become pH equilibrated.

The resulting slurry of cells and water solution was then transferred to a suitable jacketed 1.5 in. dia. reactor column to form a cell bed having a settled depth of about 40 in. (100 cm.). Minimum agitation of the slurry was employed in order to reduce any mechanical injury to the hydrated cells. A water solution having the same composition described above having a pH of 8.0 measured at 25°C. was passed at 10°–27°C. up through the cell bed at a rate of 1.3–1.5 gal./sq. ft. of bed cross-sectional area/min. The water solution was passed up through the column for about 1 hour until the outflow was clear and until the effluent pH was stabilized at 8.0 measured at 25°C. The water solution flow was then stopped. A dextrose solution described in Example 1 at 60°C. and having a pH of 7.5–8.0 measured at 60°C. was then passed up through the cell bed at a rate of 1.3–1.5 gal./sq. ft. of bed cross-sectional area/min. until the effluent solution from the bed has the same dextrose content as the entering dextrose solution. Once the dextrose solution started to enter the bed, suitable heating fluid at 60°C. was passed through the jacket of the column. The dextrose solution flow was then stopped and the cell bed was allowed to settle for about 15–20 min. During the above conditioning process, the water solution and the subsequent dextrose solution were recycled through the cell bed. The pH of the water solution and the subsequent dextrose solution being recycled were maintained, respectively, at 8 measured at 25°C. and 7.5–8.0 measured at 60°C. by the addition of sodium hydroxide.

The resulting conditioned cell bed was then used to isomerize dextrose to fructose in the manner described in Example 1 to produce an isomerized syrup containing about 42–43 weight percent fructose, having no color and containing no psicose. The above-conditioned cell bed had desirably long life.

What is claimed is:

1. A process for conditioning bacterial cells having glucose isomerase activity for subsequent use to produce a fructose-containing product which comprises
   a. mixing the bacterial cells at about 10°–27°C. with water or an aqueous dextrose solution at a pH of about 8 measured at 25°C. until the cells are hydrated and pH equilibrated; and
   b. passing an aqueous dextrose solution up through a bed of such bacterial cells at a temperature of about 60°C. and at a pH of 7.5–8.0 measured at 60°C. until the effluent solution is clear and the pH thereof is stabilized at 7.5–8.0 measured at 60°C; or passing water at a temperature of about 10°–27°C. and at a pH of 8.0 measured at 25°C. up through a bed of such bacterial cells until the effluent solution is clear and the pH thereof is stabilized at 8.0 measured at 25°C., followed by the step of passing an aqueous dextrose solution up through the bed at a temperature of about 60°C. and at a pH of 7.5–8.0 measured at 60°C. until the effluent solution has the same dextrose content as the entering dextrose solution.

2. A process according to claim 1 wherein the aqueous dextrose solution employed in steps (a) and (b) has a Dextrose Equivalent of about 97–98 and contains about 30 to 50 weight percent dissolved solids, which solids contain 93–96 weight percent dextrose.

3. A process according to claim 1 wherein the bacterial cells having glucose isomerase activity had been previously treated with glutaraldehyde.

4. A process according to claim 3 wherein the glutaraldehyde-treated cells had been previously dried and sized to be retained on a 60 mesh screen and to pass through a 20 mesh screen.

5. A process according to claim 1 wherein in step (b) the water or aqueous dextrose solution is passed up through the bed of bacterial cells at a rate of 1.3–1.5 gal./sq. ft. of bed cross-sectional area/min.

6. A process according to claim 1 wherein the water or aqueous dextrose solution contains about 0.0005 Molar concentration of cobalt, about 0.005–0.007 Molar concentration of magnesium and about 0.01 Normal concentration of citric acid.

* * * * *